United States Patent [19]

Wiley

[11] Patent Number: 4,846,200
[45] Date of Patent: Jul. 11, 1989

[54] PERIODONTAL POCKET CLEANER

[76] Inventor: Larry J. Wiley, 2644 Dwight Way #10, Berkeley, Calif. 94704

[21] Appl. No.: 458,354

[22] Filed: Jan. 17, 1983

[51] Int. Cl.$^4$ ............................................. A61C 15/00
[52] U.S. Cl. ..................................... 132/321; 132/329
[58] Field of Search ..................................... 132/89, 93

[56] References Cited

U.S. PATENT DOCUMENTS

| 106,773 | 8/1870 | Blake . | |
|---|---|---|---|
| 2,008,206 | 7/1935 | Grant | 132/89 |
| 3,563,253 | 2/1971 | Barman | 132/89 |
| 3,605,765 | 9/1971 | Canby | 132/93 |
| 3,775,848 | 12/1973 | Barnett | 132/89 |
| 3,954,115 | 5/1976 | Bengtsson | 132/89 |
| 3,999,562 | 12/1976 | Reukauf | 132/89 |
| 4,008,727 | 2/1977 | Thornton | 132/89 |
| 4,135,528 | 1/1979 | Stark | 132/89 |
| 4,304,245 | 12/1981 | Lichfield | 132/89 |

OTHER PUBLICATIONS

Periodontal Pocket Brush known to Inventor by hearsay only, no reference to Periodontal Pocket Brush known.

Primary Examiner—Richard J. Apley
Assistant Examiner—J. Welsh
Attorney, Agent, or Firm—Donald G. Lewis

[57] ABSTRACT

The periodontal pocket cleaner is a device for removing material from a periodontal sulcus or periodontal pocket and for ascertaining and monitoring bleeding and suppuration within the sulcus or pocket. The pocket cleaner is a disposable item composed of a soft hardwood or similarly appropriate wood. It has an elongated narrow shape with the grain of the wood parallel to the direction of elongation. The device tapers to a functional point at one end enabling this tapered end to be easily inserted into the sulcus or periodontal pocket. The tapered end of the pocket cleaner is softened by being moistened before being inserted into the sulcus or pocket. The tapered end of the pocket cleaner is used to scoop material from the sulcus or pocket, to scrape plaque from the tooth surfaces adjacent to the sulcus or pocket, and to absorb blood and other suspended components from the sulcus or pocket. By virtue of its small size, narrow shape, wooden composition, softness, and pliancy, the pocket cleaner minimizes the deformation and abrasion of the detached gingival tissues which form the sulcus or pocket. In spite of its small size and narrow shape, the moistened pocket cleaner usually maintains sufficient strength to clean several sulci and pockets. The absorbent wood of the pocket cleaner also provides the vehicle for the delivery of medication as a complement for the treatment of infections within the deeper recesses of pockets.

10 Claims, 2 Drawing Sheets

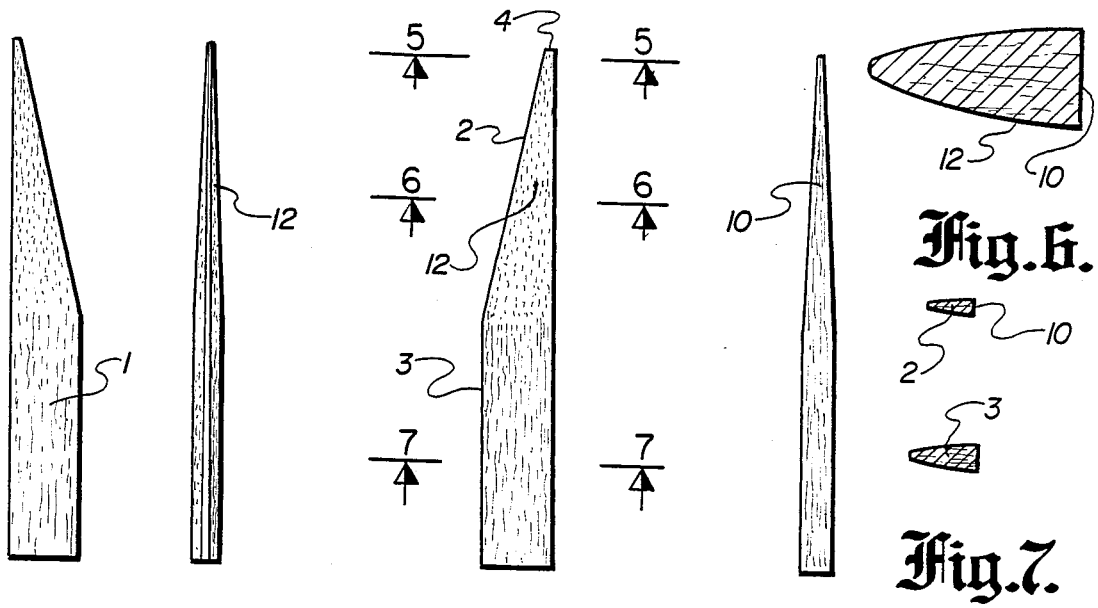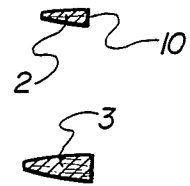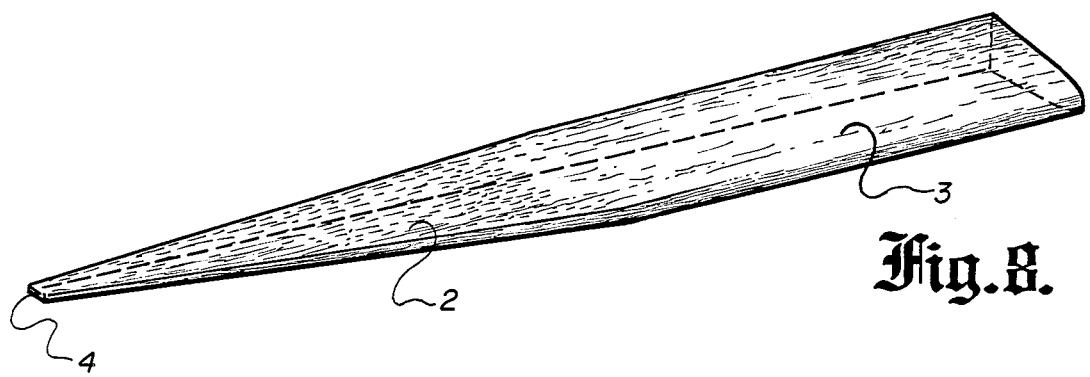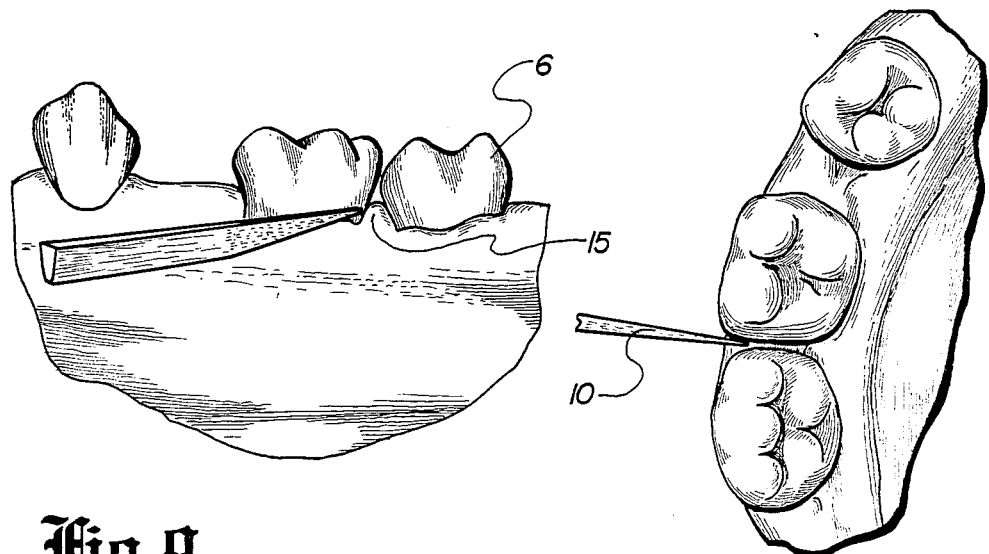

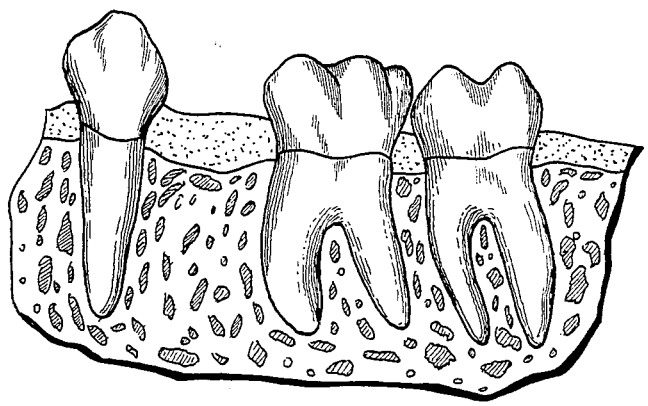
Fig.11.
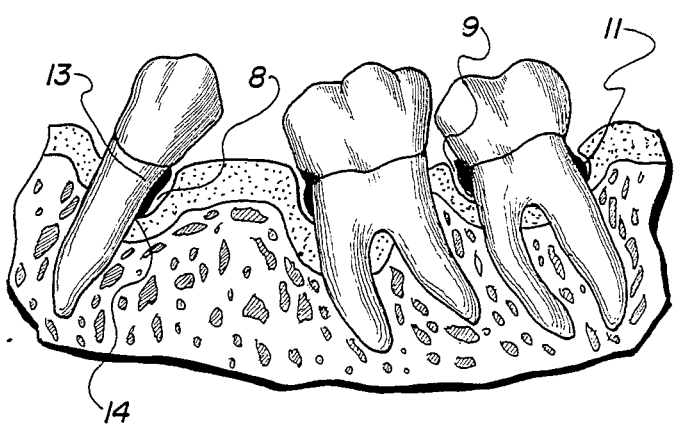
Fig.12.
Fig.13. Fig.14. Fig.15.
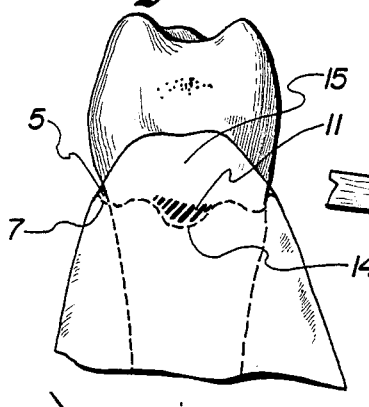 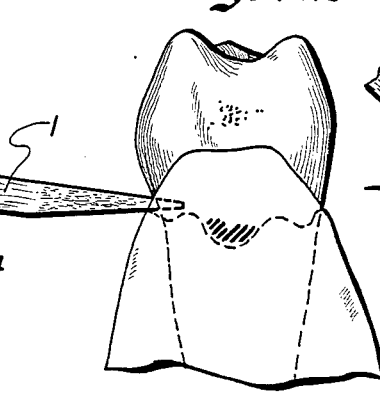 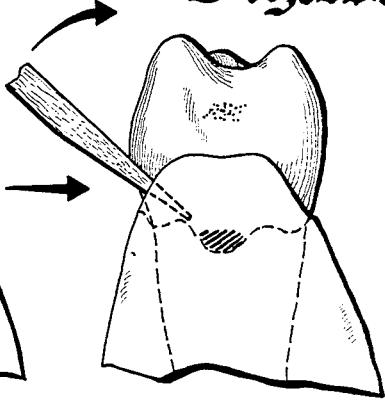
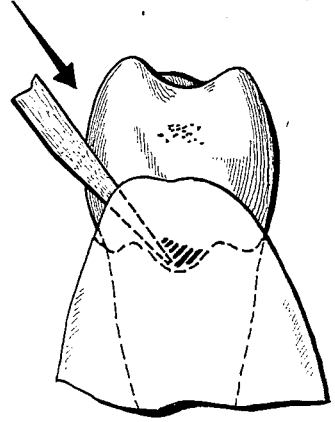 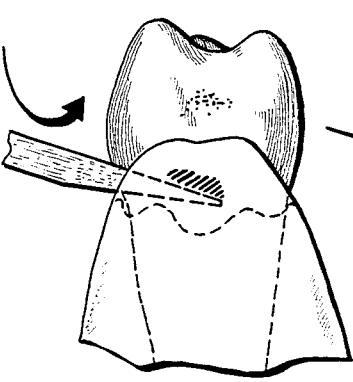 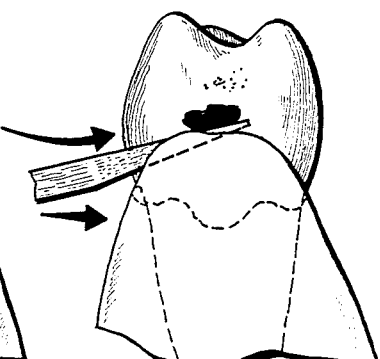
Fig.16. Fig.17. Fig.18.

PERIODONTAL POCKET CLEANER

BACKGROUND OF THE INVENTION

The periodontal pocket cleaner is a device for removing foreign material from periodontal pockets and periodontal sulci and from the tooth surfaces adjacent to such pockets and sulci. The periodontal pocket cleaner is particularly useful for removing foreign material from interdental periodontal pockets.

The gingiva of the healthy periodontium is normally attached to the tooth and gives support to the tooth. The margin of the healthy gingival attachment includes a gingival sulcus, i.e. a slight recession of the gingival attachment which results in a small detachable space between the tooth and the surrounding gingiva at the margin. A periodontal pocket occurs if the recession of the gingival attachment extends beyond the normal sulcus beyond approximately 4 mm. in depth.

The etiology of the formation of periodontal pockets is not fully understood. However, pathological sequelae to the formation of a periodontal pocket can be pernicious to the health of the periodontium. The growth and formation of bacterial plaque in the vicinity of the sulcus are a capital etiological factor in the formation of a pocket. After the periodontal pocket begins to form, the pocket will tend to accumulate more debris, including food particles. This accumulation of debris will further promote bacterial growth and bacterial plaque formation, and may lead to bacterial invasion of the gingival tissues and the excretion of bacterial toxins which can inflame the gingival tissues. The accumulation of debris and the subsequent bacterial infection within the periodontal pocket contributes to the pathological sequelae of pocket formation. The bacterial infection within a pocket can lead to the permanent resorption of the alveolar process, to the subsequent loss of support for the tooth, and to the eventual loss of the tooth itself. The bacterial infection within a pocket can also lead to apical migration of the attachment apparatus and the characteristic gum recession of periodontal disease The bacterial infection may deter reattachment of the gingiva to the tooth and may promote further detachment of the gingiva from the tooth surface, thereby progressively increasing the size and depth of the periodontal pocket, enabling the pocket to accumulate more debris, and compounding the risk of further sequelae.

Removing accumulated materials from the periodontal pocket and destroying the bacteria will ameliorate some or all of the pathological sequelae of pocket formation. Unfortunately, the anatomy of the periodontal pocket inherently limits the accessibility to the pocket. After the formation of the pocket, the detached gingiva continues to lie as a sleeve against the tooth. Any device or agent for cleaning a periodontal pocket must enter through the pocket opening and reach into the deepest sections of the pocket. Interdental periodontal pockets have particularly limited accessibility.

An interdental periodontal pocket is a pocket situated interdentally between a papilla and the proximal surface of a tooth. The proximity of the adjacent teeth spatially hinders access to an interdental pocket for cleaning. Popular prior art devices such as the tooth brush, dental floss, and gum massagers are unable to penetrate completely into or to clean deeper interdental pockets because the are not structured to permit this kind of access. The pocket cleaner is particularly efficacious for cleaning interdental periodontal pockets.

Dental floss can not reach the deeper recesses of peridontal pockets. The protocol for the use of dental floss requires that the floss first be stretched taut against a surface of a tooth in a direction approximately parallel to the gum line. The stretched floss is then moved up and down to remove material from the tooth surface. However, the movement of the floss is limited by the gingival attachment to the tooth. The recess of a pocket lies below the upper most gingival attachment and is substantially inaccessible to the cleaning action of floss. The periodontal pocket cleaner is designed to reach the recesses of a pocket which are inaccessible to floss. Flossing sensitive teeth can sometimes cause discomfort. However, scraping plaque from sensitive teeth with a moistened pocket cleaner is unlikely to cause discomfort because the cleaning surface of the pocket cleaner is soft and because the patient can directly control the pressure and course of contact between the device and the tooth.

A tooth brush may be of some utility for cleaning the lingual and labial aspects of periodontal sulci. However, action of the bristles of the tooth brush is crude for the task of cleaning pockets. The bristles may be unable to fully penetrate the deeper recesses of a periodontal pocket and action of the tooth brush as a whole is relatively indiscriminate. For cleaning interdental pockets, the utility of the tooth brush is negligible because of the spatial hindrance of the adjacent teeth.

Gum massagers are too bulky to penetrate the recesses of periodontal sulci and pockets. Gum massagers are designed to stimulate the gum and to clean tooth surfaces above the gum line. The periodontal pocket cleaner shares some structural similarities to gum massagers. However, the crucial difference between the periodontal pocket cleaner and a gum massager lies in the ability of the pocket cleaner to penetrate the recesses of the periodontal sulci and pockets. Compared to gum massagers, the pocket cleaner has a much smaller size and a much narrower shape. While the reduced size and shape of the pocket cleaner reduces its structural strength compared to gum massagers, the pocket cleaner retains sufficient strength to sweep the sulci and pockets The composition, size, and shape of the pocket cleaner are optimized for strength, but are consistant with the requirement that the pocket cleaner have access to the sulci and pockets As a consequence, if the pocket cleaner is used as a gum massager, it is somewhat less durable than the typical gum massager.

One class of prior art device which is useful for cleaning the recesses of periodontal pockets includes dental curettes. Dental curettes are metallic devices designed to be used by dental hygienists or dentists for scraping and sweeping material from periodontal pockets. Curettes are not designed for patient use. Curettes are metallic and therefore cannot absorb material from the pocket, can not deliver antiseptics to the pocket, and are prone to cause tissue damage to the gingiva due to their hardness. The pocket cleaner is distinguished from the curette because the pocket cleaner has a wooden composition; because the pocket cleaner is primarily suitable for patient use rather than clinical use; because removed blood and other pocket materials are absorbed by the pocket cleaner for better observation and for monitoring the state of pocket disease; and because the pocket cleaner can deliver medication to the pocket recess.

Another class of prior art device which is useful for cleaning the recesses of periodontal pockets includes periodontal brushes. A periodontal brush is a bristle brush with bristles attached to a twisted double wire. The assembly of bristles and twisted wire is designed to be inserted into periodontal pockets. The patient cleans his periodontal pockets by brushing out the pocket material. Because of the differences in composition between the periodontal brush and the wooden periodontal pocket cleaner, they have markedly different properties. The soft hardwood of the pocket cleaner is absorbant and pliant so as not to damage the detached, frequently inflamed, gingival tissues surrounding the pocket; the soft hardwood also absorbs liquid materials including blood from the pocket in order to facilitate the observation of periodontal pathologies and to monitor the state of disease and inflamation of the pocket; the soft hardwood can also be used to deliver medication to the pocket recess; the soft hardwood pocket cleaner is a disposable. The bristles of the periodontal brush cause the brush to be less effective for sweeping along the gingival attachment line than the wooden pocket cleaner.

Toothpick devices share some similarities with the periodontal pocket cleaner. Both devices can be wooden and both devices may be used for cleaning tooth surfaces. However, tooth pick devices are adapted for dislodging food which is jammed between two teeth, while the pocket cleaner is adapted for scraping attached bacterial plaque from the root surface and sweeping loose material from pockets and sulci. Because tooth picks require considerable force to dislodge food jammed between two teeth, they require substantial structural strength and durability. Because of this, tooth picks are relatively large and hard and are therefore inappropriate for cleaning sulci and pockets. Because of its specilized function, the periodontal pocket cleaner lacks the size, strength, and durability of the tooth pick.

SUMMARY OF THE INVENTION

The periodontal pocket cleaner is a device to be used by dental patients having a condition of periodontal pockets. The periodontal pocket cleaner should be used by dental patients having a diseased condition within their periodontal pockets due to poor periodontal hygiene; by individuals wishing to maintain the hygiene of periodontal pockets; and by individuals wishing to maintain the hygiene of their healthy periodontal sulcus. Because of time and expense, the typical periodontal patient can make only periodic visits to a clinic to have periodontal pockets cleaned and treated. The dental patient uses the pocket cleaner principally for home care to maintain the health of pockets between visits to the dental clinic. After each meal, the patient should manipulate the pocket cleaner to remove material from pockets. The pocket cleaner may be particularly useful for the home care of dental patients who have undergone peridontal surgery or who are candidates for peridontal surgery due to periodontal disease resulting in part from the formation of pockets.

The patient probes the pocket with the pocket cleaner and sweeps material from the pocket. The pocket cleaner has a tapered end with a functional point which sweeps through the pocket. As it sweeps through the pocket, the pocket cleaner scoops material from the pocket and scrapes plaque and other attached material from the adjacent tooth surfaces.

The pocket cleaner is preferably made from a soft hardwood or a wood of like properties. The best known composition is a basswood (Tilia). The wood is cut along the grain so that the grain is parallel to the direction of elongation of the device in order to maximize its strength and to avoid splintering. The pocket cleaner has a tapered end which has a size and shape which enables the patient to insert the device into periodontal pockets without undue deformation of the detached gingival tissues which surround the pocket.

The patient moistens the tapered end of the pocket cleaner with saliva before using the device. The soft hardwood becomes more pliant after it is moistened. However, it retains sufficient strength to sweep the pocket and to scrape the plaque which is attached to the adjacent tooth surface. Softness and pliancy are required in order to avoid damaging the surrounding gingiva when the pocket cleaner sweeps the pocket and scrape plaque from the adjacent tooth surfaces. The gingival tissues which surround and border the pocket can be inflamed and sensitive due to a pathology. However, the pocket cleaner does not deform or damage these tissues because of its size and shape and because of its softness and pliancy.

The wooden pocket cleaner absorbs blood and other liquids as it sweeps the pocket. Besides enhancing the ability to remove material from the pocket, the absorbency of the pocket cleaner enables the patient to monitor the health of the pockets. If the patient finds blood or pus on the pocket cleaner after sweeping a pocket, the patient has an indication of a diseased active site process.

The pocket cleaner can also act as a carrier for the delivery of medications, including antiseptics and antibiotics, for the treatment of diseased pockets. Either the manufacturer or the patient may load the wooden pocket cleaner with a medication which can be absorbed by the wooden composition for delivery to the pocket when the pocket cleaner is moistened.

Because of its shape, size, and pliancy, the pocket cleaner does not damage the detached gingival tissue surrounding the pocket. The pocket cleaner is suitable for frequent daily usage for as long as the interdental pocket persists.

The pocket cleaner is a disposable item. The pocket cleaner may be mass produced cheaply because of the relatively low cost of materials and manufacture. The disposability of the pocket cleaner makes it convenient. But more importantly, the disposability of the pocket cleaner promotes good hygiene in the treatment of diseased pockets by allowing the user to discard the device after each use and to use a clean new device for the next pocket. Using a clean new device for each pocket, particularly after cleaning a diseased pocket, will help to prevent cross contamination caused by the transfer of pocket materials from a pathological pocket to an other pocket.

The periodontal pocket cleaner is novel because it is the first device to be used by the patient for removing material from the deeper recesses of periodontal pockets by means of scraping and scooping.

The periodontal pocket cleaner is novel because it is the first device to be used by the patient for removing material from the deeper recesses of periodontal pockets by means of sweeping, scooping, scraping, and absorbing.

The periodontal pocket cleaner is novel because it is the first device for daily home use by the dental patient which can act as a carrier for the delivery of medications to the deeper recesses of periodontal pockets.

The periodontal pocket cleaner is novel because it is the first wooden device which can be used by the dental patient to monitor the state of health of deeper recesses of periodontal pockets by observing the presence or absence of blood or pus absorbed by the device after cleaning a pocket.

The periodontal pocket cleaner is novel because it is the first disposable device for the cleaning of periodontal pockets.

The periodontal pocket cleaner is novel because it is the first periodontal device to combine the function of a cleaner and a carrier.

The periodontal pocket cleaner is novel because it is the first wooden device to combine the function of a cleaner and disease monitor.

The periodontal pocket cleaner is novel because it is the first wooden device to combine the functions of a cleaner, a disease monitor, and a carrier.

BRIEF DESCRIPTION OF THE DRAWINGS

FIG. 1 is an orthographic view of a preferred embodiment of the periodontal pocket cleaner, showing the handle end and the tapered end with its functional point and scraping surface.

FIG. 2 is a second orthographic view of the pocket cleaner of FIG. 1 rotated 90 degrees about the direction of elongation, showing the handle end and the tapered end with the scraping surfaces on either side.

FIG. 3 is a third orthographic view of the pocket cleaner of FIG. 1 rotated 180 degrees about the direction of elongation, showing the handle end and the tapered end with its functional point and scraping surface.

FIG. 4 is a forth orthographic view of the pocket cleaner of FIG. 1 rotated 270 degrees about the direction of elongation, showing the handle and the tapered end with the scoop surface.

FIG. 5 is an enlarged sectional view of the pocket cleaner of FIG. 3, enlarged ten fold, the section taken proximate to the functional point and showing the semielliptical shape of the functional point FIG. 6 is a sectional view of the pocket cleaner of FIG. 3, the section taken approximately in the center of the tapered end and showing the semielliptical profile of a section of the tapered end, including the scraping surfaces and the scoop surface.

FIG. 7 is a sectional view of the pocket cleaner of FIG. 3, the section taken approximately in the center of the handle end and showing the semielliptical profile of a section of the handle end.

FIG. 8 is an enlarged view in perspective of the pocket cleaner of FIG. 1.

FIG. 9 is a reduced view in perspective of the pocket cleaner of FIG. 1 and a vestibular view of three teeth and their associated periodontium, showing the functional point of the pocket cleaner pointing towards a papilla and an interdental space; showing the scoop surface oriented approximately parallel to the occlusal plane and normal to the adjacent tooth surface; and showing the scraping surface approximately parallel to the adjacent tooth surface.

FIG. 10 is an alternate view in perspective of the three teeth, the periodontium, and a fragment of the pocket cleaner of FIG. 9, the view rotated 90 degrees from the view in FIG. 9, showing the top of the teeth and showing the fragment of the tapered end of the pocket cleaner touching an interdental tooth surface.

FIG. 11 is a sectional view of the periodontium and three teeth of FIG. 9, showing the periodontium in a state of health without pockets.

FIG. 12 is a sectional view of the periodontium and three teeth of FIG. 9, showing the periodontium with interdental pockets and with plaque and debris or other foreign material within the pockets.

FIGS. 13, 14, 15, 16, 17, and 18 are each a sectional view of the periodontium and one tooth from FIG. 10 showing the protocol for sweeping material from an interdental pocket.

FIG. 13 shows the tooth and associated periodontium and indicates the boundary of gingival attachment to the tooth; shows the interdental pocket; and shows the plaque or other foreign material contained within the pocket.

FIG. 14 shows the pocket cleaner oriented parallel to the occlusal plane and inserted between the papilla and the tooth with the functional point of the pocket cleaner within the sulcus and proximate to the boundary of gingival attachment to the tooth and with the tapered end resting on the marginal gingiva.

FIG. 15 shows the pocket cleaner rotated 45 degrees from the occlusal plane with the functional point contacting the boundary of gingival attachment to the tooth.

FIG. 16 shows the pocket cleaner translated into the recesses of the pocket with the functional point following the boundary of gingival attachment at the bottom of the pocket recess.

FIG. 17 shows the pocket cleaner sweeping through the pocket, scooping material from the pocket, and scraping plaque and other adhering material from the adjacent tooth surface.

FIG. 18 shows the pocket cleaner removing material from the pocket and preparing to remove the material from the interdental space.

DESCRIPTION OF THE PREFERRED EMBODIMENT

The periodontal pocket cleaner (1) is a piece of wood with an elongated shape. The pocket cleaner (1) has a tapered end (2) and a handle end (3). The tip of the tapered end (2) forms a functional point (4). The functional point (4) of the tapered end (2) is inserted into the periodontal sulcus (5) associated with a tooth (6) at the marginal gingiva (7) and thence into the pocket (8). The tapered end (2) is approximately 1.8 cm long. This length is optimal for cleaning typical pockets (8) in the normal adult human mouth. The handle end (3) is approximately 1.6 cm long for the hand held device. The lengths of either end of the device have been optimized to conform to anatomical constraints inherent in the mouth. The tapered end (2) must be long enough to reach down into the deeper recesses of interdental pockets (9). The handle end (3) must be long enough to enable the user's fingers to easily grasp and control the device within the mouth. The device must be short enough to fit easily between the cheek and the gums for cleaning interdental pockets (9) of rear molars from a buccal aspect. Otherwise, the device tends to protrude excessively into the cheek when these rear molars are cleaned. Also, an excessively long handle end (3) encumbers the user's control of the device. Alternatively, the device may be held by a brace. If a brace is used, the length of the handle end (3) is adapted to conform to the brace in addition to the anatomical constraints.

The tapered end (2) of the pocket cleaner (1) is adapted to sweep through the periodontal pocket (8). Sectional views of the tapered end (2) and functional point (4) are illustrated in FIGS. 5 and 6. The profiles of these sectional views approximate a solid semiellipse, bisected along its minor axis. Perspective views in FIGS. 9 and 10 illustrate the scoop surface (10) corresponding to the minor axis of the semiellipse shown in the sectional views. This scoop surface (10) may extend the entire length of the tapered end (2) and continue onto the handle end (3). When the tapered end (2) is inserted into a pocket (8), the scoop surface (10) is oriented in the foreward direction so as to catch material (11) as it advances across the pocket (8). FIGS. 9 and 10 illustrate the scoop surface (10) in the proper orientation. FIGS. 17 and 18 illustrate material (11) which has been pushed from the pocket (8) and caught by the scoop surface (10). The scoop surface (10) is very narrow at the functional point (4) of the tapered end (2) and becomes progressively wider towards the handle end (3). The width of the scoop surface (10) is minimized in order to minimize the deformation of the pocket anatomy during the sweep.

The tapered end (2) also has a scraping surface (12) which slides along the surface of the tooth (6) and scrapes off materials (11) which adhere to the tooth (6). FIGS. 8 and 9 illustrate perspective views of the scraping surfaces (12). FIGS. 5 and 6 illustrate sections of the tapered end (2), including profiles of the scraping surfaces (12). The profile of the scraping surfaces (12) may have an approximately elliptical curvature. FIGS. 16 and 17 illustrate the tapered end sweeping through the pocket and scraping plaque and other adherent materials (11) from tooth surfaces (13) adjacent to the pocket. During the sweep, the scraping surface (12) is pressed laterally against the adjacent tooth surface (13) as it slides across the pocket (8). The ability of the device to transfer lateral pressure from the scraping surface (12) to the adjacent tooth surface (13) is limited by the strength of the tapered end (2). The strength of the tapered end (2) is limited because of its small thickness and its wooden composition. Excessive pressure will cause the tapered end (2) to bend or to break. On the one hand this strength limitation of the tapered end (2) shortens the useful life of the device; on the other hand, this strength limitation has the important advantage that the sensitive gingival tissues which surround the pocket (8) are protected from inadvertant physical trauma due to the application of excessive lateral pressures.

The tapered end has greater strength for supporting the stress of the sweep than for supporting lateral pressure. The dimension corresponding to the major axis of the semiellipse imparts strength to the tapered end for supporting the stress of the sweep. The dimension corresponding to the minor axis supports the lateral pressure. Still, the dimension of the major axis must be small at the functional point (4) to enable the tapered end (2) to clean around the bottom of narrow recesses in the periodontal pocket (8) near the area of the boundary (14) of the gingival attachment to the tooth (6). The dimension of the major axis becomes progressively greater in sections taken progressively further from the functional point (4). The dimensions of the major and minor axes of the tapered end (2) are adapted to balance the need for accessibility to the pocket (8) with the need for mechanical strength. If the pocket cleaner (1) is squeezed and scraped clean after each sweep, it will usually have sufficient strength and durability to clean several pockets (8) before breaking or bending.

To commence the use of the pocket cleaner (1), the patient first moistens the tapered end (2) including the functional point (4) in order to soften the wood. Typically, the patient moistens the device with saliva. Next, holding the handle end (3) of pocket cleaner (1) with the fingers, the patient inserts the pocket cleaner (1) at The marginal gingiva (7), sliding the functional point (4) gently underneath the gum and into the gingival sulcus (5).

FIG. 14 shows the approach for inserting the pocket cleaner (1) into an interdental area. The patient slides the functional point (4) underneath the papilla (15) and into the interdental sulcus (5) or interdental pocket (9). The tapered end may initially rest on the marginal gingiva (7). If an interdental pocket (9) is to be cleaned, the angle of entry of the tapered end (2) is rotated with respect to the occlusal plane so as to excede the steepest slope of the boundary (14) of gingival attachment within the interdental pocket (9). FIG. 15 shows rotation of the angle of approach for the pocket cleaner (1) for insertion into the recess of the interdental pocket (9). It is usually best to sweep interdental areas both from a vestibular approach and from a lingual approach.

As the patient eases the pocket cleaner (1) into the sulcus (5), the patient may discover that the sulcus (5) is shallow and that there is little or no pocket. In this case, the patient sweeps along the bottom boundary (14) of the sulcus with the functional point (4), catching and removing debris and other materials (11) from the sulcus (5) with the scoop surface (10) of the device. Simultaneously, the patient scrapes the adjacent tooth surface (13) with the scraping surface (12) of the device to remove baterial plaque and other adherent materials (11). The patient relies on tactile sensation during this sweeping process in order to guide the functional point (4) of the device along the bottom of the sulcus (5). However, a novice patient may also wish to use a mirror to help guide the device while learning its proper use.

During this process, the patient should remove captured and absorbed materials (11) from the tapered end (2) of the device after each sweep. Typically, the patient may squeeze captured and absorbed materials (11) from the soiled device by passing the device between the frontal incisors or between the fingernails under pressure. Captured and absorbed materials (11) should be squeezed from both the scraping surface (12) and the scoop surface (10). If the tapered end (2) of the device is broken or fatigued, or if the function point is blunted or excessively frayed, the device has lost its utility and should be replaced. If, however, the tapered end (2) of the used device has retained sufficient shape and strength, the device may then be used for cleaning the next sulcus (5) or pocket (8), unless, perhaps, the device has been soiled by diseased pocket material.

The protocol for cleaning periodontal pockets (8) is similar to the protocol for cleaning the sulcus (5). However, in order to sweep the entire pocket (8), the patient should rotate the angle of approach of the device and insert as much of the tapered end (2) as is necessary in order to the reach the deepest recess of the pocket (8). FIGS. 16 and 17 illustrate the sweeping of a pocket (9). In the case of very deep pockets (8), the patient may need to incline the pocket cleaner (1) to an angle which is almost normal to the occlusal plane. This means that the functional point (4) may be pointing vertically down from the occlusal plane for mandibular teeth and vertically up from the occlusal plane for maxillary teeth with very deep pockets.

As in the protocol for sweeping the sulcus (5), the patient relies on tactile sensation while sweeping a pocket in order to maintain contact between the functional point (4) of the device and the bottom boundary (14) of the pocket (8). While sweeping through the pocket (8), the device catches material (11) on its scoop surface (10) and removes the material (11) from the pocket (8). Lateral pressure is exerted on the device while sweeping the pocket (8) in order to scrape bacterial plaque and other adhering material (11) from the adjacent surface (13) of the tooth. Such adhering material (11) rides on the scraping surface during the sweep and is removed from the pocket (8). Liquids within the pocket (8) ar absorbed by the device and thereby removed from the pocket (8). The patient should repeat the sweeping process three or four times or until the area feels smooth or clean. Oftentimes, it may be necessary to clean the device between sweeps of the same pocket (8). The device should be visually checked for adhering material (11) before proceeding to the next pocket (8).

In the case of interdental pockets (9) between large molars, spatial hindrance may limit the course of the sweep. In these cases, the patient should first enter the space from the labial aspect to perform the procedure and then repeat the procedure entering the space from the lingual aspect, i.e. from within the arc of the teeth.

Since the pocket cleaner (1) will absorb blood or pus within the pocket (8), the pocket cleaner (1) can be used to monitor the presence of blood or pus within the pocket (8). The presence of blood or pus on the tapered end (2) of the pocket cleaner (1) may indicate to the patient that there is a diseased state within the pocket (8).

I claim:

1. A periodontal pocket cleaner for sweeping through a periodontal pocket having deep recesses and for cleaning material from the deep recesses of the pocket and from tooth surfaces adjacent to the pocket, the periodontal pocket cleaner comprising:

a tapered end having a scoop surface, a scraping surface, and a functional point, and a handle end connected to said tapered end for inserting and sweeping said tapered end within the pocket, said tapered end having a shape, dimensions, and a composition for imparting sufficient strength, softness, and pliancy to said tapered end for enabling, for at least one time, said tapered end to be inserted into the deep recesses of the pocket, to sweep across the deep recesses of the pocket, and to remove material from the deep recesses of the pocket and the adjacent tooth surfaces without causing clinically significant risk of damaging tissues proximal to the pocket, whereby sweeping said tapered end across the pocket cleans the pocket by causing the scoop surface to scoop material from the deep recesses of the pocket and causing the scraping surface to scrape material from the adjacent tooth surfaces, and whereby the composition, the shape, and the dimensions of said tapered end are combined and adapted for imparting the strength, softness, and pliancy of said tapered end.

2. A periodontal pocket cleaner as in claim 1 wherein the periodontal pocket includes an interdental periodontal pocket.

3. A periodontal pocket cleaner as in claim 1 wherein the composition of said tapered end imparts an absorbancy for enabling said tapered end to absorb materials from the pocket, whereby sweeping said tapered end across the pocket cleans the pocket by causing said tapered end to absorb material from the deep recesses of the pocket.

4. A periodontal pocket cleaner as in claim 3 additionally for delivering a medication to the deep recesses of the periodontal pocket, wherein the absorbancy of said tapered end including a capacity to absorb the medication prior to insertion of said tapered end into the pocket and a capacity for desorbing and delivering the medication within the pocket, whereby said tapered end acts as a carrier for delivering the medication to the deep recesses of the periodontal pocket.

5. A periodontal pocket cleaner as in claim 3 additionally for detecting bleeding and thereby for providing an indicator of inflamation within the deep recesses of the pocket, wherein said tapered end having a color contrasting with the color of blood and the absorbancy of said tapered end including an absorbancy for blood, whereby the absorption of blood by said tapered end after insertion into the deep recesses of the pocket provides an inferential indication of inflamation within the deep recesses of the pocket, 6. A periodontal pocket cleaner as in claim 1 wherein the composition of said tapered end including a soft hardwood.

7. A periodontal pocket cleaner as in claim 6 wherein the shape of said tapered end is elongated with the grain of the soft hardwood running substantially parallel to the direction of elongation, whereby said tapered end is rendered strong and pliable and splintering of the soft hardwood is minimized.

8. A periodontal pocket cleaner as in claim 1 wherein the scoop surface running substantially parallel to the direction of elongation, which is substantially normal to the tooth surface when said tapered end is inserted into the pocket, and which is adapted to catch and to scoop material for removing the material from the pocket when said tapered end is swept through the pocket and the scraping surface also running substantially parallel to the direction of elongation, which is substantially parallel to the surface of the tooth when said tapered end is inserted into the pocket and which is adapted for scraping away material adhering to the surface of the tooth when said tapered end is swept through the pocket while pressing against the tooth surface.

9. A periodontal pocket cleaner as in claim 8, wherein the dimension of said tapered end in the direction of elongation is approximately 1.8 centimeters; the dimension of the scoop surface orthoganal to the direction of elongation declines with the taper from approximately 2.0 millimeters at the connection to said handle end to approximately 0.5 to 0.75 millimeters at the functional point; the dimension of the scraping surface orthoganal to the direction of elongation declines with the taper from approximately 4.0 millimeters at the connection to said handle end to approximately 0.5 to 1.0 millimeters at the functional point; and said handle end is approximately 16 centimeters long.

10. A method for cleaning material from an interdental periodontal pocket using an interdental periodontal pocket cleaner having a tapered end composed of a soft hardwood with a functional point, a scoop surface, and a scraping surface, the soft hardwood having a color which contrasts with the material from the pocket and acting as a carrier for delivering medication to the pocket, the method comprising:

positioning the functional point of the pocket cleaner at the marginal gingiva of the pocket with the scoop surface facing away from the marginal gingiva and the scraping surface facing the tooth surface, inserting the tapered end into the pocket so that the functional point continually contacts the boundary of attachment between the free gingival tissue and the adjacent tooth, while the scraping surface contacts and scrapes the adjacent tooth surface, sweeping the tapered end across the deep recesses of the pocket keeping the functional point in continual contact with the boundary of attachment between the free gingival tissue and the adjacent tooth as long as possible while scraping material from the tooth surface, catching material in the scoop surface, the soft hardwood absorbing material from the pocket and delivering medication to the pocket, removing the pocket cleaner from the pocket together with the captured and absorbed material, examining the removed material for the purpose of monitoring of the presence and absence of blood within the pocket, the presence of blood indicating a state of pathology.

* * * * *